United States Patent
Copp et al.

(10) Patent No.: US 8,275,441 B2
(45) Date of Patent: Sep. 25, 2012

(54) ELECTRODES POSSESSING CHANGE INDICATOR

(75) Inventors: Warren Copp, Chicopee, MA (US); Erick Garstka, Westfield, MA (US); Christopher Hyatt, South Hadley, MA (US); Kathleen Tremblay, Westfield, MA (US); Peter Meyer, Shrewsbury, MA (US); Scott Coggins, Palmer, MA (US); Lee Burnes, Wilbraham, MA (US); David Selvitelli, Suffield, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 960 days.

(21) Appl. No.: 12/261,134

(22) Filed: Oct. 30, 2008

(65) Prior Publication Data
US 2009/0270710 A1 Oct. 29, 2009

Related U.S. Application Data

(60) Provisional application No. 60/984,869, filed on Nov. 2, 2007.

(51) Int. Cl.
*A61B 5/04* (2006.01)
*A61N 1/04* (2006.01)
*H01B 1/12* (2006.01)

(52) U.S. Cl. ........ 600/396; 600/395; 600/372; 600/391; 600/392; 607/152; 607/153; 252/519.33

(58) Field of Classification Search .................. 600/382, 600/392, 395, 396; 252/500, 510
See application file for complete search history.

(56) References Cited

U.S. PATENT DOCUMENTS

| | | | | |
|---|---|---|---|---|
| 4,391,278 A | * | 7/1983 | Cahalan et al. | 600/391 |
| 4,768,523 A | | 9/1988 | Cahalan et al. | |
| 6,272,364 B1 | * | 8/2001 | Kurnik | 600/345 |
| 6,328,910 B1 | * | 12/2001 | Askill et al. | 252/299.7 |
| 6,444,214 B1 | * | 9/2002 | Cole et al. | 424/401 |
| 6,987,133 B2 | | 1/2006 | Chen | |
| 2003/0055478 A1 | | 3/2003 | Lyster et al. | |
| 2003/0199783 A1 | * | 10/2003 | Bloom et al. | 600/549 |
| 2005/0136077 A1 | | 6/2005 | Yahiaoui et al. | |
| 2005/0277991 A1 | | 12/2005 | Covey et al. | |
| 2006/0161097 A1 | * | 7/2006 | Domb | 604/20 |
| 2007/0282188 A1 | | 12/2007 | Copp-Howland | |
| 2007/0282408 A1 | | 12/2007 | Coggins | |

(Continued)

FOREIGN PATENT DOCUMENTS

EP 0 904 779 3/1999

(Continued)

OTHER PUBLICATIONS

Search Report from corresponding European Application No. EP 10 16 0096 mailed Apr. 4, 2011.
International Search Report from European Application No. EP 08 25 3592 dated Mar. 6, 2009.

(Continued)

*Primary Examiner* — Lee S Cohen
*Assistant Examiner* — Erin M Cardinal
(74) *Attorney, Agent, or Firm* — Lisa E. Winsor (57) ABSTRACT

The present disclosure provides electrodes that possess components capable of indicating to an end-user when the electrode is in need of replacement. The electrode includes a substrate and a conductive composition on at least a portion of a surface of the substrate. The conductive composition includes at least one hydrogel and at least one component that precipitates from the hydrogel after repeated use of the electrode, thereby providing an indication to replace the electrode.

6 Claims, 3 Drawing Sheets

U.S. PATENT DOCUMENTS

2008/0195089 A1 * 8/2008 Thiagalingam et al. ........ 606/35

FOREIGN PATENT DOCUMENTS

| | | |
|---|---|---|
| EP | 1 133 985 | 9/2001 |
| KR | 2002 0074599 | 10/2002 |
| WO | WO 88/05666 A1 | 8/1988 |
| WO | WO 93/09713 | 5/1993 |
| WO | WO 2005/099606 A1 | 10/2005 |
| WO | WO 2007/142797 A2 | 12/2007 |

OTHER PUBLICATIONS

International Search Report from European Application No. EP 10 16 7140 dated Jul. 21, 2010.

International Search Report from European Application No. EP 10 16 7522 dated Jul. 22, 2010.

Yoshida, K. et al., "Changes in the Skin and Electrode Impedance Spectra Due to Long-Term Surface Stimulation", *Proc. Fifth Annual IFESS Conference*, 2000, 5:282-285.

\* cited by examiner

ELECTRODES POSSESSING CHANGE INDICATOR

CROSS-REFERENCE TO RELATED APPLICATIONS

This application claims the benefit of and priority to U.S. Provisional Patent Application No. 60/984,869, filed Nov. 2, 2007, the entire disclosure of which is incorporated by reference herein.

TECHNICAL FIELD

The present disclosure relates to hydrogels suitable for use as conductive compositions, methods of making these compositions, and the use of these compositions with medical electrodes.

BACKGROUND OF RELATED ART

Hydrogels constitute a broad class of materials which may be completely water soluble or swell extensively in water but are not completely water soluble. They have been used in a variety of biomedical applications and may be applied in bulk forms which vary from clear to opaque, and from a relatively stiff to a relatively soft consistency. Sometimes the bulk forms are reinforced by reinforcement members which may be woven or non-woven fabrics to increase the composite strength and/or dimensional stability. Hydrogels have also been used as coatings for various biomedical applications.

Medical electrodes are used to transmit electrical signals or currents between the body of a patient and external medical equipment. These electrodes may include a conductive composition adhered to or otherwise in contact with, the skin of the patient, and a conductor, which is electrically connected to the conductive composition and to the external medical equipment.

Hydrogels for use as conductive compositions with medical electrodes remain desirable.

SUMMARY

The present disclosure provides electrodes that possess components capable of indicating to an end-user when the electrode is in need of replacement. In embodiments, an electrode of the present disclosure may include a substrate and a conductive composition on at least a portion of a surface of the substrate, the conductive composition including at least one hydrogel and at least one component having a limited solubility in water that precipitates from the hydrogel after repeated use of the electrode thereby providing an indication to replace the electrode.

In other embodiments, an electrode of the present disclosure may include a substrate and a conductive composition on at least a portion of a surface of the substrate, the conductive composition including at least one hydrogel and at least one thermochromic material which will change its color or opacity on exposure to heat thereby providing an indication to replace the electrode.

In yet other embodiments, an electrode of the present disclosure may include a substrate and a conductive composition on at least a portion of a surface of the substrate, the conductive composition including at least one hydrogel and at least one ionic component that may be iontophoretically delivered from the hydrogel after repeated use of the electrode thereby providing an indication to replace the electrode.

In yet other embodiments, an electrode of the present disclosure may include a substrate, a conductive composition on at least a portion of a surface of the substrate, the conductive composition including at least one hydrogel, and a heat sensitive component on a portion of a surface of the substrate opposite the surface of the substrate having the conductive composition that will provide an indication to replace the electrode on exposure to heat.

Methods for producing electrodes and the components thereof are also provided, as are methods for their use.

DETAILED DESCRIPTION

Any adhesive application, including those involving tissue, are within the purview of the hydrogel compositions of the present disclosure. In embodiments, hydrogels may be utilized as adhesives and/or conductive compositions for medical electrodes. The hydrogels of the present disclosure may include components that provide an indication to an end-user that the hydrogel is reaching the end of its useful life and, thus, the electrode should be replaced.

As used herein, the term "hydrogel" may refer to a wide variety of polymer-based compositions. These materials may be synthesized for example from monomer(s) or from monomer(s) mixed with polymer(s) or cross-linked polymer solutions in water. They may be obtained by chemical modification of existing polymer(s) or by adding water to existing dry polymers.

Any biocompatible hydrogel may be utilized in accordance with the present disclosure. Generally speaking, a hydrogel according to the present disclosure may include a coherent, three-dimensional aqueous polymer system capable of imbibing water without liquefying. In embodiments, insolubility in water may be provided by crosslinking the hydrogel polymer. In embodiments, hydrogels or water-containing gels of the present disclosure may include water and various chemical substances including gelatin; polysaccharides; crosslinked acrylamide polymers, hydroxyethylmethacrylate polymers; crosslinked polyhydroxyethylacrylate; polymerized, crosslinked 2-acrylamido-2-methylpropane sulfonic acid polymers or one of their salts such as the sodium or potassium type; crosslinked polyvinylpyrrolidone; polyacrylic acid; copolymers of the aforementioned monomers with each other, copolymers of the aforementioned monomers with other polymers such as polystyrene or other non-hydrogel-forming polymers, one or more salts of the foregoing, and combinations thereof.

For example, by cross-linking homopolymers of an acrylamide derivative such as 2-acrylamido-2-methylpropanesulfonic acid or one of its salts, hydrogels may be formed. Copolymers thereof may also be formed in the same way with acrylamide. Cross-linked homopolymers of acrylic acid and of methacrylic acid, their salts and copolymers thereof do likewise, as do other acrylic cross-linked homopolymers and copolymers.

Hydrogels of the present disclosure derive their adhesive properties in part from their ability to absorb water. When a relatively dry body of hydrogel contacts moisture, such as the moisture in tissue, particularly internal tissue, or any other moist surface, it develops an aggressive adhesive nature. When the polymer of the hydrogel is crosslinked to an adequate degree, the bulk hydrogel is strong enough, even when swelled with additional liquid, to provide adhesive support for pacing leads, thereby establishing extended connection of the lead to tissue.

Excessive crosslinking decreases the tack of the hydrogel. Too little crosslinking decreases its cohesive strength. Thus, in embodiments, a crosslinking agent may be utilized in forming the polymer suitable as a hydrogel of the present disclosure.

In use, a hydrogel of the present disclosure may contain the polymer or copolymer, and any other additives, including components utilized to form the copolymer, in an amount from about 20% by weight to about 97% by weight of the hydrogel, with the balance being water and/or a humectant.

In some embodiments, a suitable hydrogel for use as a conductive composition may include a copolymer. Non-limiting examples of suitable copolymers may include a first monomer, such as a mixture of acrylic acid and a salt thereof, and a second monomer, such as one of more monomers selected from $CH_2=CHC(O)XR$, in which X is O or NH and R is an unsubstituted or substituted alkyl group of 1 to 5 carbon atoms. The hydrogel may also include water; an electrolyte or mixture of electrolytes; a polymerization initiator; a neutralizer such as sodium hydroxide; optionally, a crosslinking agent; and optionally, a thickener.

In embodiments, a first monomer which may be used to form a copolymer for use in a hydrogel includes acrylic acid, a salt thereof, or a mixture thereof. The copolymer thus produced by polymerization includes acid acrylate moieties ($-CO_2H$ and/or $-CO_2M$, in which M is a cation such as sodium ion, potassium ion, lithium ion, ammonium or substituted ammonium ion, etc.) directly attached to the polymer backbone.

In embodiments, a copolymer utilized in a hydrogel of the present disclosure may include a second monomer which may be one of more monomers selected from $CH_2=CHC(O)XR$, in which X is O or NH and R is an unsubstituted or substituted alkyl group of 1 to 5 carbon atoms. The polymer produced by this polymerization includes groups of the structure $-C(O)XR$ directly attached to the polymer backbone.

Suitable unsubstituted alkyl groups are methyl, ethyl, n-propyl, n-butyl, and n-pentyl. Suitable substituents that may be present in a substituted alkyl group are halo (such as F, Cl, or Br) cyano, carboxylic acid and salts thereof (i.e., $-CO_2H$ or $-CO_2M$, in which M is a cation), phosphate and salts thereof, and sulfonic acid and salts thereof. An example of such a substituted alkyl group is (3-sulfopropyl)acrylic acid ester, potassium salt. Suitable second monomers include 2-acrylamido-2-methylpropane sulfonic acid ($CH_2=CH-CONHC(CH_3)_2-CH_2-SO_3H$) and/or a salt thereof. Suitable salts include the sodium, lithium, potassium, ammonium, and substituted ammonium salts, and mixtures thereof.

In embodiments, the second monomer utilized in a copolymer component of a hydrogel of the present disclosure is 2-acrylamido-2-methylpropane sulfonic acid sodium salt (NaAMPS) ($CH_2=CH-CONHC(CH_3)_2-CH_2-SO_3^- M^+$). Thus, in some embodiments, the first monomer utilized in a copolymer component of a hydrogel of the present disclosure may include a mixture of acrylic acid and sodium acrylate, and the second monomer may include sodium 2-acrylamido-2-methylpropane sulfonate.

The first monomer (acrylic acid and/or salt or salt thereof, calculated as acrylic acid) may be present in an amount of from about 8 wt % to about 85 wt % of copolymer in the hydrogel, in embodiments from about 10 wt % to about 80 wt %, of the total amount of the copolymer in the hydrogel. The second monomer, in embodiments NaAMPS, may be present in an amount of from about 15 wt % to about 92 wt % of the copolymer in the hydrogel, in embodiments from about 20 wt % to about 90 wt % of the copolymer in the hydrogel.

Optionally, an effective amount of a cross-linking agent or mixture of cross-linking agents may be utilized to form the copolymer component of a hydrogel of the present disclosure. An effective amount of cross-linking agent is an amount that produces a conductive composition with the desired physical properties, such as coherence and adhesion, and electrical properties. Although the amount required will depend on, for example, the molecular weight of the cross-linking agent, the number of ethylenically unsaturated, free radical polymerizable groups present in the cross-linking agent, the amount of free radical polymerizable monomers present in the monomer mix, when the cross-linking agent is present, the amount of crosslinking agent will be present in an amount of from about 0.01 wt % to 1 wt % of the copolymer utilized in the hydrogel, in embodiments from about 0.02 wt % to 0.08 wt % of the copolymer utilized in the hydrogel.

Suitable cross-linking agents include free radical polymerizable monomers that possess more than one ethylenically unsaturated, free radical polymerizable group. Numerous crosslinking agents polymerizable by free-radical initiated polymerization are within the purview of those skilled in the art. Crosslinking agents include, for example, bis-acrylamides and methacrylamides, such as N,N'-methylene bis-acrylamide; acrylate and methacrylate esters of polyols, such as, ethylene glycol diacrylate and dimethacrylate, diethylene glycol diacrylate and dimethacrylate, trimethylolpropane triacrylate and trimethacrylate, ethoxylated trimethylolpropane triacrylate and trimethacrylate; pentaerythritol triacrylate and trimethacrylate, pentaerythritol tetraacrylate and tetramethacrylate, and polyethylene glycol diacrylates and dimethacrylates, such as the diacrylates and dimethacrylates of polyethylene glycols having a molecular weight of from about 200 to about 600. In embodiments, a suitable crosslinking agent may include N,N'-methylene bis-acrylamide $[(CH_2=CHCONH)_2CH_2]$.

In embodiments, a polymerization initiator may be utilized with the first monomer and second monomer to form a copolymer for use in a hydrogel of the present disclosure. An effective amount of a polymerization initiator may be combined with the monomers to form such a copolymer. As used herein, an effective amount is an amount that produces efficient polymerization of the monomers under polymerization conditions to produce a hydrogel suitable for use as a conductive composition. Numerous free radical polymerization initiators are within the purview of those skilled in the art. The polymerization initiator may be a single compound or a mixture of compounds. Thermal and/or photo free radical polymerization initiators, for example, may be used.

Suitable thermal free radical polymerization initiators include azo compounds, such as 2,2-azobisisobutyronitrile (AIBN). Suitable photo free radical polymerization initiators are disclosed in "Photoinitiators for Free-Radical-Initiated Photoimaging Systems," by B. M. Monroe and G. C. Weed, *Chem. Rev.*, 93, 435-448 (1993) and in "Free Radical Polymerization" by K. K. Dietliker, in *Chemistry and Technology* of *UV and EB Formulation for Coatings, Inks, and Paints*, P. K. T. Oldring, ed., SITA Technology Ltd., London, 1991, Vol. 3, pp. 59-525. Suitable free radical photo polymerization initiators include, for example, 1-hydroxycyclohexylphenyl ketone (HCPK, IRGACURE® 184); 2-hydroxy-2-methyl-1-phenylpropan-1-one (DAROCUR® 1173); 2-hydroxy-1-[4-(2-hydroxyethoxy)phenyl]-2-methyl-1-propan-1-one (IRGACURE®2959), 2,2-dimethoxy-2-phenylacetophenone (benzildimethyl ketal, BDK, IRGACURE®651), benzophenone, a mixture of 50 wt % benzophenone and 50 wt % of 1-hydroxycyclohexylphenyl ketone (IRGACURE® 500), and combinations thereof.

The polymerization initiator may be present in a copolymer utilized in a hydrogel in an amount less than about 1 wt % of the copolymer, in embodiments less than about 0.7 wt % of the copolymer, in other embodiments less than about 0.4 wt % of the copolymer.

The hydrogel of the present disclosure may also include an electrolyte or a mixture of electrolytes. The electrolyte may be a salt, such as lithium chloride, sodium chloride, potassium chloride, magnesium acetate, ammonium acetate, or a mixture thereof. In embodiments, a suitable electrolyte may include potassium chloride. The hydrogel may possess the electrolyte in an amount from about 0.5 wt % to about 10 wt % of the hydrogel, in embodiments from about 1 wt % to about 8 wt % of the hydrogel.

The hydrogel utilized as a conductive composition may also include a neutralizer. Bases such as hydroxides, amines, Lewis bases, and mixtures thereof may be used as neutralizers. Non-limiting examples of neutralizers include ammonium hydroxide, sodium hydroxide, potassium hydroxide, lithium hydroxide, combinations thereof, and the like. If the acrylic acid and/or the second monomer, such as the 2-acrylamido-2-methylpropane sulfonic acid, are included as monomers in forming a copolymer for use in the hydrogel, it may be desirable to add neutralizer to neutralize some of the acid so that the pH of the mixture is from about 3 to about 6.5.

Where utilized, a neutralizer may be present in an amount from about 2 wt % to 8 wt % of the hydrogel.

In addition to a free radical initiator, small amounts of free radical polymerization inhibitors may be present with one or more of the monomers, and/or the crosslinking agent, and/or may be added to the mixture to prevent premature polymerization of the reaction mixture. Suitable free radical polymerization inhibitors include, for example, hydroquinone, 4-methoxyphenol, di-t-butyl-p-cresol, pyrogallol, t-butyl catechol, benzoquinone, 4,4'-thio-bis-(3-methyl-6-t-butylphenol), and 2,2'-methylene-bis-(4-methyl-6-t-butylphenol). When present, the amount of the polymerization inhibitor may be from about 0.01 wt % to about 5 wt % of the hydrogel.

In some embodiments a thickener may be added to the hydrogel. Suitable thickeners include rheological modifiers which permit tailoring the viscosity of the hydrogel to permit its use as a conductive composition with a medical electrode. Non-limiting examples of such thickeners include silica, gums including xanthan gum, polymers including polyvinyl pyrrolidone (PVP), polyacrylamides, polyacrylic acid (including those sold under the name CARBOPOL®), salts thereof, combinations thereof, and the like. Where utilized, a thickener may be present in a hydrogel of the present disclosure in an amount from about 0.1 wt % to about 8 wt % of the hydrogel, in embodiments from about 0.5 wt % to about 5 wt % of the hydrogel.

Other conventional ingredients of conductive compositions may be present in the hydrogel. For example, humectants and medicinal agents, including antimicrobials, antiseptics, analgesics, disinfectants, and the like, may be added to a hydrogel.

Water is present in the mixture. The amount of water includes any water present in any of the ingredients and any water added with ingredients that are in water solution, such as the monomers, the crosslinking agent, the neutralizer, etc. In embodiments, humectants may be added to the water phase of a hydrogel utilized as a conductive composition in an electrode of the present disclosure. Humectants which may be used include non-volatile, non-toxic, water soluble or water miscible viscous liquids at room temperature. Suitable humectants include, but are not limited to, polyhydric alcohols such as glycerol, sorbitol, ethylene glycol, propylene glycol, polyethylene glycols (PEG) of varying molecular weights including PEG 300, PEG 400 and PEG 600, polypropylene glycols, combinations thereof, and the like. The humectant may be utilized in combination with water or without water. Where utilized with water, the ratio of water to humectant may be from about 1:10 to about 10:1.

As noted above, in use, a hydrogel of the present disclosure may contain the polymer or copolymer and any other additives described herein in an amount from about 20% by weight to about 97% by weight, with the balance being water and/or a humectant in an amount from about 3% to about 80% by weight of the hydrogel.

An example of a suitable polymer which may be utilized as the hydrogel includes RG-63B, commercially available from Covidien.

The monomers and any additional components described above may be mixed and spread or coated as a layer on a release liner, for example a siliconized release substrate such as silicone coated polyethylene terephthalate film, or other substrate prior to polymerization. Free radical polymerization may be initiated by, for example, heating the mixture when a thermal free radical polymerization initiator is present in the mixture, or exposing the mixture to actinic radiation when a photoinitiated free radical polymerization initiator is present in the mixture. Any convenient source or sources of actinic radiation providing wavelengths in the region of the spectrum that overlap the absorption bands of the photoinitiated free radical polymerization initiator can be used to activate polymerization. The radiation can be natural or artificial, monochromatic or polychromatic, incoherent or coherent, and for high efficiency should correspond closely in wavelengths to the absorption bands of the polymerization initiator. Conventional light sources include fluorescent lamps, mercury vapor lamps, metal additive lamps, and arc lamps. Useful lasers are those whose emissions fall within or overlap the absorption bands of the photoinitiated free radical polymerization initiator. Although, if desired, the mixture may be degassed before polymerization and/or the polymerization may be carried out under an inert atmosphere, it is not necessary to degas the mixture before polymerization or to carry out the polymerization under an inert atmosphere.

Following polymerization, the resulting conductive composition may transferred to a conductive substrate. Alternatively, the conductive composition may be adhered to a conductive substrate, and the release liner left in place to protect the conductive composition until it is ready for use.

Change Indicating Component

In accordance with the present disclosure, an electrode of the present disclosure also possesses a component which may be utilized to indicate the useful life of the hydrogel has expired or is about to expire. This indication will identify for an end-user that the electrode in use should be replaced and a new electrode should be utilized. In some embodiments, the component indicating that it is time to change or replace the electrode may be included in the hydrogel described above as part of a conductive composition. In other embodiments, the component indicating that it is time to change or replace the electrode may be a separate component applied to an electrode that is not included in the hydrogel described above.

For example, in embodiments, a salt or similar component having a limited solubility in water may be added to the hydrogel. Enough of this material is added to the hydrogel so that it all dissolves, but is very near its saturation point. This material may be opaque or possess a color. While in solution in the hydrogel, the color or opacity of the component is not observed. However, as the electrode possessing a hydrogel of the present disclosure is utilized and exposed to the atmosphere, water is lost. As more water is lost with repeated use, the concentration of the component in the remaining water of the hydrogel will reach the point of saturation, thereby becoming insoluble and precipitating out of the remaining hydrogel. The component will thus leave the solution, turning the remaining hydrogel a color or result in the hydrogel becoming cloudy or opaque.

The impedance of the electrode is directly related to the water level in the hydrogel. As water is lost from the hydrogel the impedance of the electrode increases. Thus, the precipitate that forms in the gel as water is lost, is an indirect indicator of an increase in the impedance of the electrode, and the change in clarity of the hydrogel due to color or opacity may be utilized as an indication that the electrode possessing the hydrogel should be changed.

In addition, in alternate embodiments, upon becoming opaque, a message or symbol that had been visible indicating the electrode was suitable for use could become obscured, thereby indicating it is time to replace the electrode. Any symbol that would indicate an electrode was suitable for use could be utilized. Non-limiting examples of such symbols include "G", "OK", "Use", a smiley face, combinations thereof, and the like. As the symbol becomes obscured by the change in opacity due to the precipitation of the component with limited solubility, an end-user would be provided with an indication to change the electrode.

Suitable components with limited solubility which may be utilized to indicate the need to change an electrode possessing a hydrogel include, but are not limited to, lithium oxide, boric acid, lithium carbonate, sodium tartrate dibasic dehydrate, sodium hydrogen tartrate, combinations thereof, and the like.

The component with limited solubility may be added in suitable amounts of from about 0.5% by weight of the hydrogel to about 2.5% by weight of the hydrogel, in embodiments from about 0.75% by weight of the hydrogel to about 2% by weight of the hydrogel.

Instead of a salt having limited solubility, a thermochromic material may similarly be added to the hydrogel. As noted above, as an electrode is utilized, and water is lost with repeated use, the impedance of the electrode will increase, thereby generating heat. The use of a thermochromic material, that is, a material which will change its color or opacity on exposure to heat, may be utilized as an indicator to the user that a temperature increase due to loss of impedance may be high enough to cause a thermal burn and thus the electrode should be changed.

Suitable thermochromic materials should undergo a change in color or opacity at a temperature somewhere between body temperature and a temperature at which a first degree thermal burn may occur. Suitable thermochromic materials include thermochromic pigments. Such pigments may include an electron-donating chromogenic substance, an electron-accepting substance, and a solvent which undergoes a reversible color change in response to a change in temperature. The color change which takes place may be from one color to another, from colored to colorless, or from colorless to colored. Thermochromic materials may be combined so that several temperatures in a predetermined range can be indicated by different colors.

Examples of such thermochromic materials include, but are not limited to, liquid crystals such as cholesteryl nonanoate, cyanobiphenyls, combinations thereof, and the like. Where utilized, a thermochromic material may be present in an amount from about 0.1% by weight of the hydrogel to about 10% by weight of the hydrogel, in embodiments from about 0.5% by weight of the hydrogel to about 5% by weight of the hydrogel.

In other embodiments, an ionic component not soluble in water or having very low solubility in water may be added to the hydrogel. The ionic component is added to the hydrogel to saturate the hydrogel, i.e., past its saturation point, thereby providing the hydrogel with either a color or opacity. As the electrode is used, the ionic component may be iontophoretically delivered to the patient, for example to the skin to which the electrode is attached. Thus, after repeated use, with more delivery of the ionic component, the concentration of the ionic component in the hydrogel will decrease and the hydrogel will lose its color or opacity and become clear. In this embodiment, the hydrogel becoming clear may be an indication that the electrode possessing the hydrogel should be changed.

In addition, in alternate embodiments, upon becoming clear, a message or symbol could become visible indicating it is time to replace the electrode. Any symbol that would indicate a time to change the electrode could be utilized. Non-limiting examples of such symbols include "N", "NG", "S", "Stop", "End", "Replace", a skull and cross bones, a frowning face, combinations thereof, and the like.

Suitable ionic components which may be utilized with the hydrogel include hydrocortisone acetate and the like. The ionic component may be added in suitable amounts of from about 3.5% by weight of the hydrogel to about 7.5% by weight of the hydrogel, in embodiments from about 4% by weight of the hydrogel to about 6% by weight of the hydrogel.

In yet other embodiments, a wax or other heat sensitive component may be applied to a surface of an electrode. For example, as noted above, as a hydrogel of the present disclosure dries out with repeated use, the impedance of an electrode utilizing such a hydrogel will increase, thereby generating heat in the hydrogel. A heat sensitive component with a specific melting point somewhere between body temperature and a temperature at which a first degree thermal burn may occur could be applied to the upper surface of a substrate utilized in forming an electrode, on the side of the substrate opposite the hydrogel, and located over the area where the connector (wire) contacts the hydrogel. This will be the warmest spot on the electrode. The heat sensitive component may either melt or become clear at a predetermined temperature, close to but below the temperature where a burn may occur, thereby indicating the time to change an electrode.

In embodiments, as the temperature increases, the wax or other heat sensitive component may melt or become clear, revealing some message or symbol underneath the wax or heat sensitive component that indicates it is time to replace the electrode. As described above, any symbol that would indicate a time to change the electrode could be utilized. Non-limiting examples of such symbols include "N", "NG", "S", "Stop", "End", "Replace", a skull and cross bones, a frowning face, combinations thereof, and the like.

Suitable heat sensitive components include, but are not limited to, waxes including paraffin waxes or commercially available waxes such as CARBOWAX® polyethylene glycols and methoxy polyethylene glycols, commercially available from the Dow Chemical Company.

Other suitable heat sensitive components which may be applied to a surface of an electrode include thermochromic materials, including any of the thermochromic materials described above for placement in the hydrogel. As with the wax described above, the thermochromic material may be applied to the surface of the substrate opposite the hydrogel where the connector (wire) contacts the hydrogel. As described above, the thermochromic material will change its color or opacity on exposure to heat, thereby indicating to the user that a temperature increase due to loss of impedance may be high enough to cause a thermal burn. Suitable thermochromic materials include the thermochromic materials and pigments described above for inclusion in the hydrogel itself. Thermochromic materials may be combined so that several temperatures in a predetermined range can be indicated by different colors.

Medical Electrodes

Medical electrodes transmit electrical signals or currents to or from a patient's skin and an external medical apparatus. Medical electrodes are within the purview of those skilled in the art. These electrodes may include a conductive composition such as a hydrogel of the present disclosure on a substrate. The layer of conductive composition can be adhered to or contacted with the skin of the patient. The medical electrode may also include a conductive interface that is electrically connected to the layer of conductive composition and adapted to be electrically connected to an item of external medical equipment. For many applications, the conductive composition should be sufficiently adhesive to adhere to the patient's skin, i.e., be a conductive adhesive. The configuration of the electrode and the adhesive properties required will depend on the intended application, such as whether the electrode is a transmission electrode, i.e., an electrode that sends electric currents or signals to the patient's body, or a sensing or monitoring electrode, i.e., an electrode that sends electrical signals from the patient's body to external medical equipment.

Figure 1:
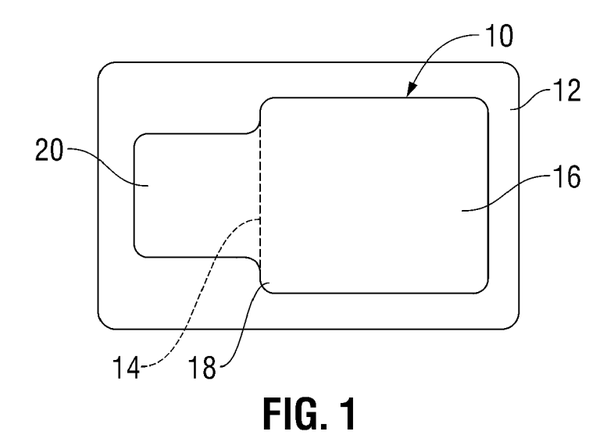
FIG. 1 is a top plan view of a medical electrode including the conductive composition of the present disclosure.
Figure 2:
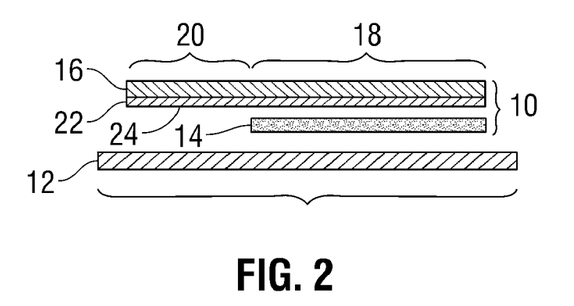
FIG. 2 is a cross-sectional view of the medical electrode of FIG. 1.

FIG. 1 and FIG. 2 show a medical electrode 10 on release liner 12. Release liner 12 is a release paper or film of a waxed or coated plastic, such as a silicone coated polyethylene terephthalate film, which may be used to protect medical electrode 10 before application of the electrode to a skin surface.

Electrode 10 includes a layer of a hydrogel of the present disclosure as conductive composition 14. Electrode 10 also includes conductive interface 16 having a conductor member with a conductive portion 18 contacting layer of conductive composition 14 and tab portion 20 extending beyond layer of conductive composition 14 for mechanical and electrical contact with external medical equipment, such as a electrocardiogram monitoring (ECG) machine, an electroencephalogram (EEG) machine, or a transcutaneous electrical nerve stimulation (TENS) machine (not shown). Conductive interface 16 includes conductive layer 24, coated on at least side 22 of conductive interface 16. Conductive layer 26 contacts layer of conductive composition 14. Medical electrode 10 can be used either as a diagnostic electrocardiogram (ECG or EKG) electrode or as a transcutaneous electrical nerve stimulation (TENS). In use, release liner 12, if present, is removed. The layer of conductive composition 14 of electrode 10 is applied to the surface of the patient's skin and electrically connected to the external medical equipment.

Figure 3:
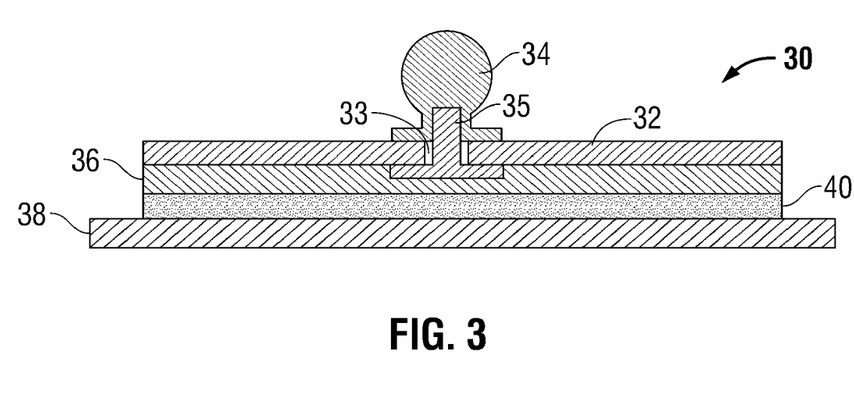
FIG. 3 is a cross-sectional view of a snap medical electrode.

FIG. 3 shows a cross-section of snap medical electrode 30 on a release liner. Electrode 30 has nonconductive backing 32, which has opening 33 covered by snap 34 through which eyelet 35 protrudes. Snap 34 is secured to eyelet 35. Together snap 34 and eyelet 35 provide at least part of a conductive interface adapted to provide an electrical connection between a flexible conductive layer 36 and the external medical equipment (not shown). Eyelet 34 and backing 32 are covered by flexible conductive layer 36 which, in embodiments, may be made of a material such as carbon vinyl. A hydrogel of the present disclosure may be utilized as a conductive composition 40 and adhered to conductive layer 36. Release liner 38 protects the conductive composition 40 prior to use. In embodiments, a complete or partial layer of silver and/or a silver salt such as silver chloride may be placed between conductive composition 40 and conductive layer 36 (not shown).

As noted above, in embodiments an electrode may have a message or symbol that either becomes visible or obscured after use, indicating it is time to replace the electrode. Such a message or symbol, in embodiments, may be placed on the surface of conductive layer 36 adjacent hydrogel 40 (not shown).

In addition, in embodiments, conductive layer 36 and nonconductive layer 32 may possess contiguous windows adjacent each other in each layer (not shown) permitting the visualization of conductive composition 40 during use so that changes in color, opacity, and the like may be observed with an electrode in place on a patient.

In other embodiments, as described above, a heat sensitive component, such as a wax or a thermochromic material, may be applied over eyelet 34 (not shown) or a portion of nonconductive backing 32 adjacent eyelet 34 (not shown). The heat sensitive component may melt, become clear, or change color after repeated use and provide an indication of when an electrode should be changed.

Figure 4:
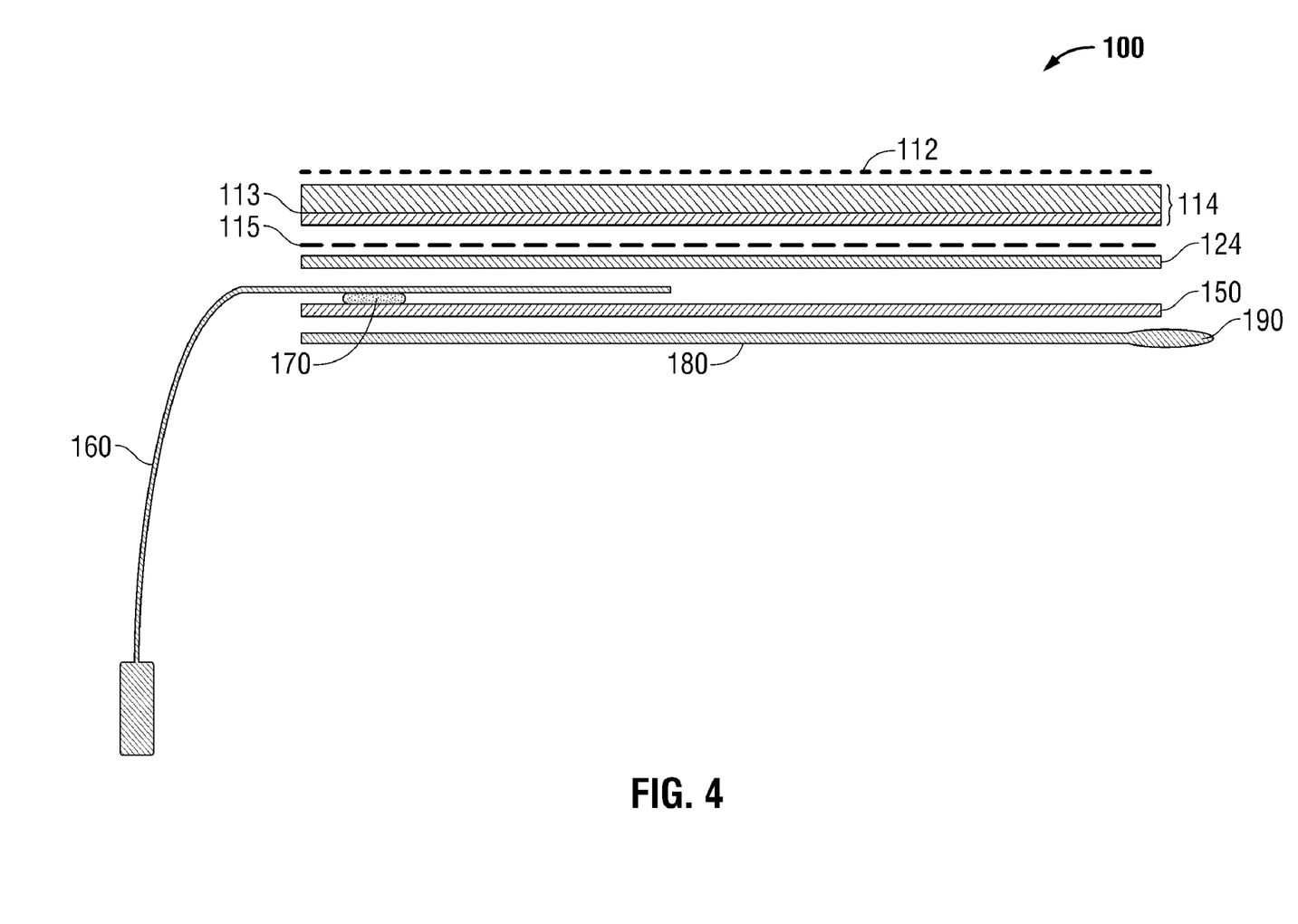
FIG. 4 is a cross-sectional view of an alternate medical electrode of the present disclosure.

FIG. 4 shows a cross-section of an alternate medical electrode 100 on a release liner 112, which may be a polyester film or any other material suitable for use as a release liner. Electrode 100 includes a layer of a hydrogel of the present disclosure, optionally possessing a change indicating component as described above, as conductive composition 114. In embodiments, conductive composition 114 may have a reinforcement member 113 embedded in the hydrogel, which may be a woven or a non-woven mesh or any other material, such as a scrim, suitable for forming a reinforcement member. Electrode 100 may also possess a conductive layer 124, which may, in embodiments, be a suitable material such as a conductive carbon film of suitable thickness, in embodiments about 2 mil. In some embodiments, a flood coat or a partial coating of silver ink 115 (which can be silver and/or silver chloride) may be between conductive layer 124 and conductive composition 114, applied as a coating on at least a portion of a surface of conductive layer 124. In embodiments, the electrode may include silver (Ag) or silver/silver-chloride (Ag/AgCl) disposed on at least a portion of the first and/or second sides of the conductive layer.

Electrode 100 may also possess a standard stainless steel or tin/copper pig tail lead wire 160 of a suitable length, in embodiments from about 5 to about 15 inches long, in other embodiments about 9 inches long. Lead wire 160 may possess an insulation jacket which, in turn, may be bound to conductive layer 124 using an adhesive 170. Electrode 100 may also possess a reinforcement film 150 having a medical grade pressure sensitive adhesive (PSA) thereon overlying lead wire 160 and affixing reinforcement film 150 to both conductive layer 124 and cover material 180. Finally, cover material 180 may possess pull tab 190 notched out of cover material 180 on the end of electrode 100 opposite the end into which the lead wire 160 enters the electrode.

Figure 5:
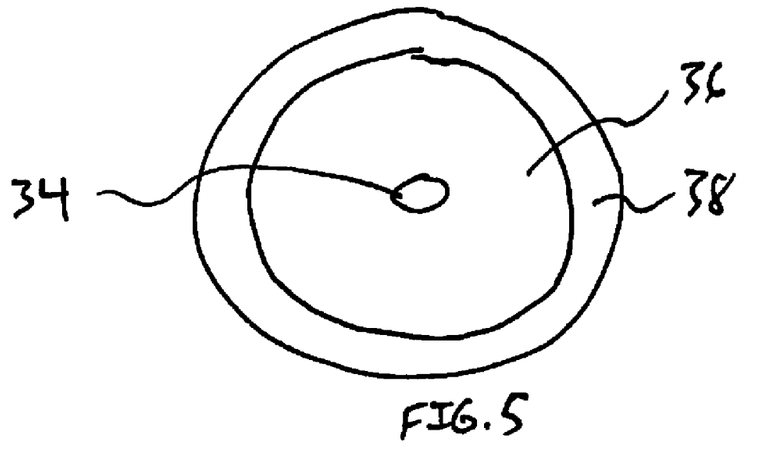
FIG. 5 is a top view of an electrode of the present disclosure prior to use.
Figure 6:
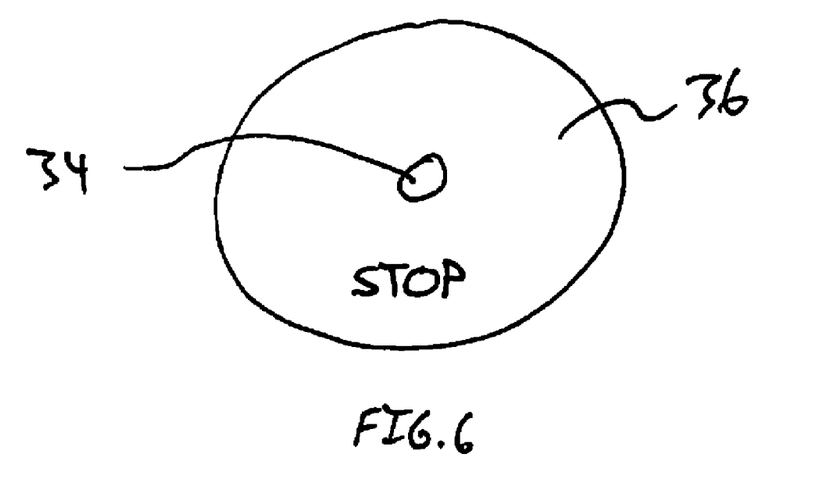
FIG. 6 is a top view of an electrode of the present disclosure after use.

FIG. 5 is a top view of an electrode of the present disclosure prior to use. From the top, flexible conductive layer 36 and overlying release liner 38, are visible. Eyelet 34 is also visible in the center of flexible conductive layer 36. FIG. 6 is a top view of an electrode of the present disclosure after use, and thus does not depict release liner 38. As can be seen in FIG. 6, a message or symbol has become visible on conductive layer 36 after use, in this case the word "STOP", indicating it is time to replace the electrode.

Medical electrodes may be packaged for use in any suitable materials within the purview of those skilled in the art. For example, electrodes may be packaged in materials such as polyethylene or other plastic films, foil barrier packaging, combinations thereof, and the like.

Industrial Applicability

The conductive compositions of the present disclosure may be useful with medical electrodes that can be used with medical equipment for a variety applications, such as: electrocardiogram monitoring (ECG) electrodes (tab and snap style) for monitoring heart activity and for diagnosing heart abnormalities; electroencephalogram (EEG) electrodes; transcutaneous electrical nerve stimulation (TENS) electrodes used for pain management; neuromuscular stimulation (NMS) used for treating conditions such as scoliosis; muscle stimulation electrodes; wound treatment electrodes (accelerated healing of skin wounds or broken bones); defibrillation electrodes to dispense electrical energy to a chest cavity of a mammalian patient to defibrillate heart beats of the patient; iontophoresis; and dispersive electrodes to receive electrical energy dispensed into an incision made during electrosurgery. Other applications of the conductive compositions of the invention include, for example, electro-surgical dispersive pads; drug delivery (passive or iontophoretic); pre-surgical limb or area markers, tapes (anchoring chest tubes, NG tubes, IVs, cannulae, etc); and sterile seals at needle or cannula entry points. The medical equipment used in these applications is within the purview of those skilled in the art.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, or material.

What is claimed is:

1. A medical electrode comprising:
   a substrate; and
   a conductive composition on at least a portion of a surface of the substrate, the conductive composition comprising at least one hydrogel and at least one thermochromic material which will change its color or opacity on exposure to heat, thereby providing an indication to replace the electrode.

2. The medical electrode of claim 1, wherein the hydrogel comprises a component selected from the group consisting of gelatin, polysaccharides, crosslinked acrylamide polymers, hydroxyethylmethacrylate polymers, crosslinked polyhydroxyethylacrylate, polymerized, crosslinked 2-acrylamido-2-methylpropane sulfonic acid polymers, crosslinked polyvinylpyrrolidone, polyacrylic acid, copolymers of the foregoing, one or more salts thereof, and combinations thereof.

3. The medical electrode of claim 1, wherein the hydrogel comprises a copolymer comprising a first monomer comprising a mixture of acrylic acid and a salt thereof, present in an amount of from about 8 weight % to about 85 weight % of the hydrogel, and a second monomer of the formula $CH_2\!=\!CHC(O)XR$, in which X is O or NH and R is an unsubstituted or substituted alkyl group of from 1 to about 5 carbon atoms present in an amount of from about 15 weight % to about 92 weight % of the hydrogel.

4. The medical electrode of claim 1, wherein the hydrogel further comprises an electrolyte present in an amount of from about 0.5% by weight to about 10% by weight of the hydrogel, and optionally a neutralizer selected from the group consisting of ammonium hydroxide, sodium hydroxide, potassium hydroxide, lithium hydroxide, and combinations thereof, optionally further comprises a cross linking agent selected from the group consisting of N-N'-methylene bisacrylamide, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylate, and combinations thereof, and optionally further comprises a polymerization initiator selected from the group consisting of 2,2-azobisisobutyronitrile, 1-hydroxycyclohexylphenyl ketone, 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof.

5. The medical electrode of claim 1, wherein the at least one thermochromic material comprises a liquid crystal selected from the group consisting of cholesteryl nonanoate, cyanobiphenyls, and combinations thereof, present in an amount of from about 0.1% by weight of the hydrogel to about 10% by weight of the hydrogel.

6. The medical electrode of claim 1, wherein the indication to replace the electrode comprises a symbol or message, and wherein the electrode optionally further comprises a conductive layer possessing a coating of silver or silver/silver-chloride on at least a portion of a surface of the conductive layer.

* * * * *